United States Patent
Burt et al.

(10) Patent No.: US 7,053,039 B2
(45) Date of Patent: May 30, 2006

(54) EFFERVESCENT CLEANING TABLETS

(75) Inventors: Diane Joyce Burt, New Windsor, NY (US); Jeanne Marie Lesica, Nutley, NJ (US); Michael Rosenstengel, Romerberg (DE)

(73) Assignee: Reckitt Benckiser Inc., Wayne, NJ (US)

( * ) Notice: Subject to any disclaimer, the term of this patent is extended or adjusted under 35 U.S.C. 154(b) by 212 days.

(21) Appl. No.: 10/475,199

(22) PCT Filed: Jan. 18, 2002

(86) PCT No.: PCT/GB02/00217

§ 371 (c)(1),
(2), (4) Date: Feb. 23, 2004

(87) PCT Pub. No.: WO02/086048

PCT Pub. Date: Oct. 31, 2002

(65) Prior Publication Data

US 2004/0116317 A1   Jun. 17, 2004

(30) Foreign Application Priority Data

Apr. 20, 2001 (GB) ................................. 0109763.3

(51) Int. Cl.
*C11D 17/00* (2006.01)
(52) U.S. Cl. ...................... 510/446; 447/422; 447/477; 447/499; 447/509
(58) Field of Classification Search ..................... None
See application file for complete search history.

(56) References Cited

U.S. PATENT DOCUMENTS 5,654,262 A    8/1997  Desai et al. ................. 510/115

FOREIGN PATENT DOCUMENTS

| DE | 19932765 | 1/2001 |
|---|---|---|
| EP | 0896053 | 2/1999 |
| EP | 1041138 | 10/2000 |
| GB | 1239641 | 7/1971 |
| GB | 2242130 | 9/1991 |
| GB | 2337055 | 11/1999 |
| GB | 2349390 | 11/2000 |
| WO | WO 97/43366 | 11/1997 |
| WO | WO 01/49818 | 7/2001 |

OTHER PUBLICATIONS

Search Report for GB0201581.6 dated Aug. 13, 2002.
Search Report for GB0109763.3 dated Oct. 10, 2001.
International Search report for PCT/GB02/00217 dated Apr. 17, 2002.

*Primary Examiner*—Necholus Ogden
(74) *Attorney, Agent, or Firm*—Norris McLaughlin & Marcus PA

(57) ABSTRACT

The present invention relates to household cleaning compositions and, in particular, to household cleaning and/or disinfecting compositions in compressed form for use in cleaning and/or disinfecting hard surfaces. An effervescent agent is used in conjunction with a germicidal agent so as to provide a cleaning and/or disinfecting composition useful in treating hard surfaces.

14 Claims, No Drawings

EFFERVESCENT CLEANING TABLETS

BACKGROUND OF THE INVENTION

The present invention relates to household cleaning compositions and, in particular, to household cleaning and/or disinfecting compositions in compressed form for use in cleaning and/or disinfecting hard surfaces.

Liquid and powdered products for cleaning and/or disinfecting hard surfaces are known in the art and are available in the marketplace. The liquid cleaning and/or disinfecting products generally contain water, thus making them heavy. Similarly, powdered products generally have a high-bulk capacity, which also results in a bulky product. Moreover, liquid and powdered cleaning and/or disinfecting products require a great deal of storage space.

Cleaning and/or disinfecting compositions in compressed form, like that of the present invention, have several advantages over such liquid and powdered products. Because they are compressed and contain no water, the tablets are light-weight and have a low-bulk capacity. Their small size makes for more economical shipping and storage.

Surprisingly, it has been found that a household cleaning and/or disinfecting compositions that effectively clean and/or disinfect hard surfaces can be prepared in compressed form (such as, for example, tablets, rings, disks, stars, spheres, sticks, pellets, ribbons, and briquettes) by combining an effervescent agent (comprising an acidic component and a basic component) with a germicidal agent into a tablet. The tablet can then be placed into a bucket of water (or other suitable vessel) to form a composition suitable for cleaning a variety of hard surfaces (for example, countertops, floors, walls, sinks, toilets, bathtubs, and the like). The compressed form cleaner of the present invention dissolves quickly, resulting in a product with little or no residue in the vessel in which it is dissolved (for example, bucket) without the loss of disinfecting and/or sanitizing properties of the germicidal agent. Preferably, the compressed form will disintegrate within about one minute after being placed in a vessel containing water, but longer times of disintegration, for example, two to twenty minutes are also acceptable.

Generally, the compressed form cleaner includes an effervescent agent, a germicidal agent, and, optionally one or more components selected from the group consisting of non-ionic surfactants, amphoteric surfactants, zwitterionic surfactants, lubricants, colorants, perfumes, deodorizers, preservatives, dyes, disintegrants, binders, absorbents, and fillers.

Preferably, the compressed form cleaner will comprise an effervescent agent, a germicidal agent, and non-ionic surfactant. More preferably, the compressed form cleaner will comprise an effervescent agent, a germicidal agent, non-ionic surfactant, and disintegrant. The compressed form cleaner is preferably of a form selected from tablets, rings, disks, stars, spheres, sticks, pellets, ribbons, and briquettes.

Effervescent Agent:

The presence of the effervescencing agent in the compressed form cleaner helps to disintegrate the form so as to disperse the germicidal agent in the form into the vessel in which the form, and water, are added. Disintegration occurs when the effervescing agent is added to water, causing a chemical reaction to release gas, carbon dioxide, which forces the other compressed materials within the compressed form away from each other, causing dispersion of the materials within the vessel. Once effervescence is ended, the resulting solution is then available for cleaning the surface intended. The generation of carbon dioxide increases the rate of solution of the other components and produces a solution in which the active ingredient, for example a germicidal agent, is homogeneously dissolved.

The effervescing agent is typically made up of two components: an acidic component and a basic component. When expose to water, these components react to form a gas (for example, carbon dioxide)

The acidic component useful in the tablet cleaner of the present invention is selected from the group consisting of an organic acid, for example a carboxylic acid, organic acid salts, organic acid anhydrides, inorganic acids, inorganic acid salts, and mixtures thereof. Preferably, the organic acid, and related salts and anhydrides are selected from carboxylic acids having up to 8 carbon atoms such as, for example acetic, formic, propionic, malic, tartaric, citric, glycolic, maleic, fumaric, adipic, succinic, lactic, gluconic, and butyric acids and their homologs, and sulphamic acid. Examples of inorganic acid or acid salts include boric acid, sodium dihydrogen phosphate, disodium dihydrogen pyrophosphate, and sodium acid sulfite. Those of ordinary skill in the art will appreciate that under certain conditions, the type of acid component to be used will depend upon the germicidal active substance to be incorporated into the compressed form such that the acid will not affect the activity or efficacy of the germicidal active substance.

The acidic component is present in the effervescent agent in an amount ranging from about 20% to about 80%, preferably from about 20% to about 60% and more preferably between about 20% to about 40%.

The basic component is selected from the group consisting of carbonates, bicarbonates, sequicarbonates and mixtures thereof. Preferably, any ammonium, alkali metal or alkali earth metal (for example, sodium, potassium, lithium, calcium, magnesium) carbonate, bicarbonate, sequicarbonates or mixtures thereof may be used in the tablet cleaner of the present invention. Potassium and sodium bicarbonate are preferred since they readily react with the acidic component of the effervescent agent to release an abundant amount of carbon dioxide as well as having good water solubility.

The basic component is present in the effervescent agent in an amount between about 10% to about 80%. Preferably, the basic component ranges in an amount from about 20% to about 70% and more preferably between about 25% and about 70%.

The acidic and basic components are included in amounts to achieve rapid, complete solubility of the tablet. Consequently, the molar ratio of acid component to basic component should be approximately within a range of from about 1.0:2.0 to about 1.0:4.0.

The combination of acidic and basic components should comprise about 50% of the weight of the tablet. Preferably, the acidic and basic components comprise at least 75% of the weight of the tablet and most preferably, at least 80% of the weight of the tablet.

The components that comprise the effervescent agents should be very dry as moisture can affect the performance of effervescence, making the compressed form unusable or cause it to disintegrate very slowly. Ideally, the effervescent agents, and the rest of the components should be used, and the final compressed form should be stored, at a temperature of less than room temperature (~25 C) and at a relative humidity of less than 20%.

Compounds that have disinfecting or sanitizing properties include cationic surfactants, biguanides, and phenolics. With the use of these materials, the materials must either be in powder form or if liquid, absorbed onto a carrier such that after doing so, the material now is a powder.

Cationic surfactants are found to provide a broad antibacterial or sanitizing function in the present invention. Any cationic surfactant which satisfies these requirements, provided they are in powder form or are absorbed onto a carrier so as to be in powder form, may be used and are considered to be within the scope of the present invention, and mixtures of two or more cationic surfactants may also be used. Cationic surfactants are well known, and useful cationic surfactants may be one or more of those described for example in *McCutcheon's Detergents and Emulsifiers*, North American Edition, 1998; *Kirk-Othmer, Encyclopedia of Chemical Technology*, 4th Ed., Vol. 23, pp. 478–541, the contents of which are herein incorporated by reference.

Examples of preferred cationic surfactant compositions useful in the practice of the instant invention are those which provide a germicidal effect to the concentrate compositions, and especially preferred are quaternary ammonium compounds and salts thereof, which may be characterized by the general structural formula:

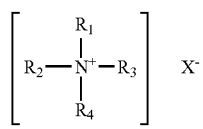

where at least one of $R_1$, $R_2$, $R_3$ and $R_4$ is a alkyl, aryl or alkylaryl substituent of from 6 to 26 carbon atoms, and the entire cation portion of the molecule has a molecular weight of at least 165. The alkyl substituents may be long-chain alkyl, long-chain alkoxyaryl, long-chain alkylaryl, halogen-substituted long-chain alkylaryl, long-chain alkylphenoxyalkyl, arylalkyl, etc. The remaining substituents on the nitrogen atoms other than the above mentioned alkyl substituents are hydrocarbons usually containing no more than 12 carbon atoms. The substituents $R_1$, $R_2$, $R_3$ and $R_4$ may be straight-chained or may be branched, but are preferably straight-chained, and may include one or more amide, ether or ester linkages. The counterion X may be any salt-forming anion which permits water solubility of the quaternary ammonium complex.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pryridinium halides such as N-cetyl pyridinium bromide, and the like. Other suitable types of quaternary ammonium salts include those in which the molecule contains either amide, ether or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylphenyltrimethyl ammonium chloride, chlorinated dodecylbenzyltrimethyl ammonium chloride, and the like.

Preferred quaternary ammonium compounds which act as germicides and which are found to be useful in the practice of the present invention include those which have the structural formula:

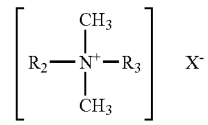

wherein $R_2$ and $R_3$ are the same or different $C_8$-$C_{12}$ alkyl, or $R_2$ is $C_{12-16}$ alkyl, $C_{8-18}$alkylethoxy, $C_{8-18}$alkylphenoxyethoxy and $R_3$ is benzyl, and X is a halide, for example chloride, bromide or iodide, or is a methosulfate or saccharinate anion. The alkyl groups recited in $R_2$ and $R_3$ may be straight-chained or branched, but are preferably substantially linear.

Examples of quaternary ammonium compounds which are either in powder form or are absorbed onto a carrier include BTC2125M P40 (alkyl dimethyl benzyl ammonium chloride and alkyl dimethyl ethylbenzyl ammonium chloride absorbed on urea), BTC 824 P-100 (alkyl dimethyl benzyl ammonium chloride), and Barquat MS-100. (alkyl dimethyl benzyl ammonium chloride).

Useful quaternary compounds are available under the BARDAC®, BARQUAT®, HYAMINE®), LONZABAC®, BTC®), and ONYXIDE® trademarks, which are more fully described in, for example, McCutcheon's Functional Materials (Vol. 2), North American Edition, 2000, and the respective product literature from the suppliers identified below. Although in liquid form, they can be placed on carriers to form a powder as discussed below.

For example, BARDAC® 205M is described to be a liquid containing alkyl dimethyl benzyl ammonium chloride, octyl decyl dimethyl ammonium chloride; didecyl dimethyl ammonium chloride, and dioctyl dimethyl ammonium chloride (50% active) (also available as 80% active (BARDAC® 208M); described generally in McCutcheon's as a combination of alkyl dimethyl benzyl ammonium chloride and dialkyl dimethyl ammonium chloride); BARDAC® 2050 is described to be a combination of octyl decyl dimethyl ammonium chloride/didecyl dimethyl ammonium chloride, and dioctyl dimethyl ammonium chloride (50% active) (also available as 80% active (BARDAC® 2080)); BARDAC® 2250 is described to be didecyl dimethyl ammonium chloride (50% active); BARDAC® LF (or BARDAC® LF-80), described as being based on dioctyl dimethyl ammonium chloride (BARQUAT® MB-50, MX-50, OJ-50 (each 50% liquid) and MB-80 or MX-80 (each 80% liquid) are each described as an alkyl dimethyl benzyl ammonium chloride; BARDAC® 4250 and BARQUAT® 4250Z (each 50% active) or BARQUAT® 4280 and BARQUAT® 4280Z (each 80% active) are each described as alkyl dimethyl benzyl ammonium chloride/ alkyl dimethyl ethyl benzyl ammonium chloride. Also, HYAMINE®) 1622, described as diisobutyl phenoxy ethoxy ethyl dimethyl benzyl ammonium chloride (50% solution); HYAMINE® 3500 (50% actives), described as alkyl dimethyl benzyl ammonium chloride (also available as 80% active (HYAMINE® 3500–80); and HYAMINE® 2389 described as being based on methyldodecylbenzyl ammonium chloride and/or methyldodecylxylene-bis-trimethyl ammonium chloride. (BARDAC®), BARQUAT®) and HYAMINE®) are presently commercially available from Lonza, Inc., Fairlawn, N.J.). BTC® 50 NF (or BTC®) 65 NF) is described to be alkyl dimethyl benzyl ammonium chloride (50% active); BTC® 99 is described as didecyl dimethyl ammonium chloride (50% active); BTC®) 776 is described to be myristalkonium chloride (50% active); BTC® 818 is described as being octyl decyl dimethyl ammonium chloride, didecyl dimethyl ammonium chloride, and dioctyl dimethyl ammonium chloride (50% active) (available also as 80% active (BTC®) 818-80%)); BTC® 824 and BTC® 835 are each described as being of alkyl dimethyl benzyl ammonium chloride (each 50% active); BTC®) 885 is described as a combination of BTC® 835 and BTC® 818 (50% active) (available also as 80% active (BTC® 888)); BTC® 1010 is described as didecyl dimethyl ammonium chloride (50% active) (also available as 80% active (BTC® 1010-80)); BTC® 2125 (or BTC® 2125 M) is described as alkyl dimethyl benzyl ammonium chloride and alkyl dimethyl ethylbenzyl ammonium chloride (each 50% active) (also available as 80% active (BTC® 2125 80 or BTC® 2125 M)); BTC®) 2565 is described as alkyl dimethyl benzyl ammonium chlorides (50% active) (also available as 80% active (BTC® 2568)); BTC® 8248 (or BTC® 8358) is described as alkyl dimethyl benzyl ammonium chloride (80% active) (also available as 90% active (BTC® 8249)); ONYXIDE® 3300 is described as n-alkyl dimethyl benzyl ammonium saccharinate (95% active). (BTC® and ONYXIDE® are presently commercially available from Stepan Company, Northfield, Ill.). Polymeric quaternary ammonium salts based on these monomeric structures are also considered desirable for the present invention. One example is POLYQUAT®), described as being a 2-butenyldimethyl ammonium chloride polymer. Other cationic surfactants suitable for use in the present invention are also set forth in the Examples below.

As mentioned above, if the quaternary ammonium compounds are in liquid form, they need to be absorbed on to a carrier so that they become a powder. Suitable carriers include those mentioned below as fillers or bulking agents, carbonates, urea and the like, provided that carrier does not affect the activity of the quaternary ammonium compounds.

Another material having disinfecting or sanitizing properties include polymeric materials which have antimicrobial activity such as, for example, ?-4-[1-tris(2-hydroxyethyl) ammonium-2-butenyl]poly[1-dimethylammonium-2-butenyl]-?-tris(2-hydroxyethyl) ammonium chloride. Preferred polymeric compounds include polymeric biguanides and their salts of the formula

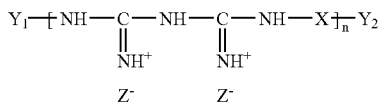

or water soluble salts, where X is any aliphatic, cyclbaliphatic, aromatic, substituted aliphatic, substituted aromatic, heteroaliphatic, heterocyclic, or heteroaromatic compound, or a mixture of any of these, and $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these, where n is an integer equal to or greater than 1, and wherein Z is an anion such as Cl? or OH?. A preferred polymeric compound is polyhexamethylene biguanide, available from Avecia as Vantocil 100.

In addition, the polymeric biguanides described in U.S. Pat. No. 4,652,585, U.S. Pat. No. 3,428,576, Great Britain Patent Specification No. 702,268, and European Patent Application 485 07943 may be used in the present invention.

Phenolic based germicidal agents can also be used in the present invention and those of ordinary skill in the art will take certain factors into consideration when selecting an appropriate phenolic in view of a proposed effervescent agent system. This selection process is well within the skill of an ordinary person. As with the quaternary ammonium compounds, if the phenolics are not in powder form, they need to be absorbed on to a carrier to then become in powder form. Examples of phenolic based germicidal agents include hexachlorophene, tetrachlorophene, 2,3 dihydroxy-5,5'-dichlorodiphenyl-sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine, dichlorophene, chlorbutanol, glyceryl laurate, halogenated diphenyl ethers, 2,4,4'-trichloro-2'-hydroxy-diphenyl ether (Triclosan® or TCS), 2,2'-dihydroxy-5,5'-dibromo-diphenyl ether, phenolic compounds, phenol, 2-methyl phenol, 3-methyl phenol, 4-methyl phenol, 4-ethyl phenol, 2,4-dichlorophenol, p-nitrophenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols, p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-isopropyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol, 2-diethylmethyl-3,5-dimethyl p-chlorophenol, 6-sec-octyl-3-methyl p-chlorophenol, o-benzylphenol, p-chloro-o-benzylphenol, 4-phenolsulfonic acid cresols (o-, m-, p-), p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, chlorothymol, phenoxyethanol, phenoxyisopropanol, 5-chloro-2-hydroxydiphenylmethane, resorcinol and its derivatives, resorcinol, methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, 4'-bromo 2,4-dihydroxydiphenyl methane, bisphenolic compounds, 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl) sulphide, bis(2-hydroxy-5-chlorobenzyl) sulphide, benzoic esters parabens such as methylparaben, propylparaben, butylparaben, ethylparaben, isopropylparaben, isobutylparaben, benzylparaben, sodium methylparaben, sodium propylparaben, halogenated carbanilides, 3,4,4'-trichlorocarbanilides (Trichlocarban® or TCC), 3-trifluoromethyl-4,4'-dichlorocarbanilide, and 3,3',4-trichlorocarbanilide.

Surfactants which can be used in the present invention are selected from the group consisting of amphoteric, anionic and nonionic surfactants and mixtures thereof. The nonionic surfactants may be straight-chain or branched and are preferably ethoxylated for increased water solubility. Nonionic surfactants are well known in the detergency art.

They may be included in the compositions of the present invention together with the other components defined hereinabove. Nonlimiting examples of suitable nonionic surfactants which may be used in the present invention are as follows:

(1) The polyethylene oxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

(2) The condensation products of aliphatic alcohols with from about 1 to about 60 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms). One example of such a nonionic surfactant is available as Empilan KM 50.

(3) Alkoxy block copolymers, and in particular, compounds based on ethoxy/propoxy block copolymers. Polymeric alkylene oxide block copolymers include nonionic surfactants in which the major portion of the molecule is made up of block polymeric $C_2$–$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

$$\text{HO-(EO)}_x\text{(PO)}_y\text{(EO)}_z\text{-H} \qquad (A)$$

where

EO represents ethylene oxide,

PO represents propylene oxide, y equals at least 15, $(EO)_{x+y}$ equals 20 to 50% of the total weight of said compounds, and, the total molecular weight is preferably in the range of about 2000 to 15,000. These surfactants are available under the PLURONIC tradename from BASF.

Another group of nonionic surfactants appropriate for use in the new compositions can be represented by the formula (B):

$$\text{R-(EO,PO)}_a\text{(EO,PO)}_b\text{—H} \qquad (B)$$

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000–5000.

Still further useful nonionic surfactants containing polymeric butoxy (BO) groups can be represented by formula (C) as follows:

$$\text{RO-(BO)}_n\text{(EO)}_x\text{—H} \qquad (C)$$

wherein

R is an alkyl group containing 1 to 20 carbon atoms, n is about 5–15 and x is about 5–15.

Also useful as the nonionic block copolymer surfactants, which also include polymeric butoxy groups, are those which may be represented by the following formula (D):

$$\text{HO-(EO)}_x\text{(BO)}_n\text{(EO)}_y\text{-H} \qquad (D)$$

wherein n is about 5–15, preferably about 15, x is about 5–15, preferably about 15, and y is about 5–15, preferably about 15.

Still further useful nonionic block copolymer surfactants include ethoxylated derivatives of propoxylated ethylene diamine, which may be represented by the following formula:

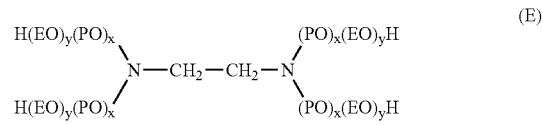

(E)

where (EO) represents ethoxy, (PO) represents propoxy, the amount of $(PO)_x$ is such as to provide a molecular weight prior to ethoxylation of about 300 to 7500, and the amount of $(EO)_y$ is such as to provide about 20% to 90% of the total weight of said compound.

Amphoteric surfactants may also be used in the present invention. Amphoteric surfactants are those surfactants whose acidic or basic character is pH dependent. Depending on the pH, amphoteric surfactants may behave either as an anionic surfactant, a cationic surfactant, or both. Preferably the amphoteric surfactants are water soluble betaine surfactants. Examples of suitable betaine surfactants are dodecyidimethylammonium acetate, tetradecyldimethylammonium acetate, hexadecyldimethylammonium acetate, alkyldimethylammonium acetate, dodecyldimethylammonium butanoate, tetradecyldimethylammonium butanoate, hexadecyldimethylammonium butanoate, dodecyldimethylammonium hexanoate, tetradecyldiethylainmonium pentanoate, tetradecyldipropylammonium pentanoate, dodecylethylammounium acetate, dodecyldimethylammonium hexanoate, and hexadecyldimethylammonium hexanoate. Preferred amphoteric betaine surfactants include, but are not limited to, lauramidopropyl betaine and cocomido betaine.

Those of ordinary skill in the art will appreciate that the use of anionic surfactants may depend upon the type of germicidal agent used in the compressed form. For example, if cationic surfactants are used, typical anionic surfactants should not be used. However, one class of anionic surfactants A further class of surfactants which may be advantageously included in the inventive compositions are carboxylates, particularly one or more alkylpolyoxycarboxylates including alkyletherpolyoxycarboxylates, or alkylarylpolycarboxylates. Exemplary alkylpolyoxycarboxylates and alkylarylpolycarboxylates include alkyl- and alkylaryl-carboxylates which include those which may be represented by the general formula:

wherein R is a straight or branched hydrocarbon chain containing from about 9 to 21 carbon atoms, and which may also include an aromatic ring, especially a phenyl group as part of the hydrocarbon chain, and M is a metal or ammonium ion.

Further examples of particularly useful carboxylate surfactants include compounds according to the formula:

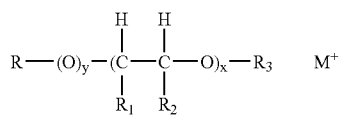

where:
R is a $C_4$–$C_{22}$ linear or branched alkyl group which may optionally include at least one aryl group, preferably $C_8$–$C_{15}$ linear or branched alkyl group which may include at least one aryl group, and yet more preferably a $C_{12-15}$ linear or branched alkyl group which may include at least one aryl group;
x is an integer from 1 to 24,
y is or 1,
$R_1$, $R_2$ and $R_3$ are each individually a group selected from H, lower alkyl radicals including methyl and ethyl radicals, carboxylate radicals including acetate and propionate radicals, succinate radicals, hydroxysuccinate radicals, or mixtures thereof wherein at least one $R_1$, $R_2$ or $R_3$ is a carboxylate radical; and,
$M^+$ is a counterion including an alkali metal counterion (i.e., sodium, potassium) or ammonium counterion.

Free acid forms of the alkylethercarboxylate compounds noted above may also be used.

Examples of such presently available commercial preparations include SURFINE WLG (Finetex Inc., Elmwood Park N.J.), SANDOPAN DTC (Clariant Chem. Co., Charlotte N.C.) in salt forms, and in free acid forms include those marketed under the tradename NEODOX (Shell Chemical Co., Houston Tex.). An example of such a carboxylate is one which is represented by the formula:

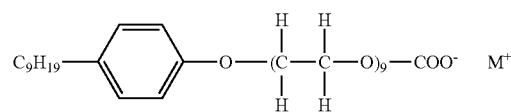

Such a material is presently commercially available under the tradename Emol®, and specifically as Emcol® CNP-110.

If cationic surfactants are not used as the germicidal agent in the compressed form, then typical anionic surfactants known to those skilled in the art, such as those described in, for example, *McCutcheon's Detergents and Emulsifiers*, North American Edition, 1998; *Kirk-Othmer, Encyclopedia of Chemical Technology*, 4th Ed., Vol. 23, pp. 478–541, can be used with the compressed form of the present invention.

The compressed form of the present invention also contains a binder and/or disintegrant. Use of a binder helps to hold the tablet together, thus enabling it to be made using a lower compaction pressure and making it inherently more likely to disintegrate well in the wash liquor. If the binder is also a material that causes disruption when contacted with water (in which case it is a disintegrant), even better disintegration properties may be achieved when used with the effervescing agent.

Materials which can be binders and/or disintegrants include organic materials such as starches, for example, corn, maize, rice and potato starches and starch derivatives, such as carboxymethyl starch, modified or pregelatinized starch and sodium starch glycolate; celluloses and cellulose derivatives, for example, sodium carboxymethyl cellulose, cross-linked modified cellulose, and microcrystalline cellulosic fibres; natural gums (for example, acacia, tragacanth, carrageenan, xanthan, agar, guar, locust bean, karaya, pectin, gellan); sugars (for example, glucose, sucrose); and various synthetic organic polymers, notably polyethylene glycol, polyvinylalcohol, polyvinylacetate and crosslinked polyvinyl pyrrolidone, and crosslinked polyacrylic acid. Inorganic swelling disintegrants include bentonite clay. It will also be appreciated that such material can also be filler material for the compressed form.

The binder/disintegrant is preferably used in an amount within the range of from 0.1 to 10 wt %, more preferably from 1 to 5 wt %.

Lubricants, which prevent the compressed form from sticking to the form press, can be added in amounts up to about 0.5%. Suitable lubricants include polyethylene glycol and boric acid, talc, colloidal silicas and the like Perfumes, dyes, and colorants are optional materials in the compressed form and when used, may be present in an amount of up to about 5 weight percent of the composition for perfume and up to about 2 weight percent of the composition for dyes and colorants. Those of ordinary skill in the art will appreciate that the type and amount of perfume, dye, and colorant used in the present invention will be of the type and in the amount so as not to have a deleterious affect on the compressed form. In addition, if any perfume, dye or colorant is in liquid form, it will have to be absorbed onto a carrier so as to make it a powder.

Those of ordinary skill in the art will appreciate that some components, for example, binders, may have properties of, for example, a disintegrant when placed within the compressed form. In addition, additional materials can be incorporated into the compressed form, for example, fillers (for example, zeolites, lactose, phosphates (with which certain disintegrants (for example, Acusol 771) is useful)), absorbers (a useful example of which is Microsponge, which is a polymer in addition to silica gels, alumina gels, and the like), and the like, the use and identification of which are well known to those of ordinary skill in the art.

Examples of compositions of the present invention, compressed into tablets, are set forth below in Table 1. The compressed forms were made under standard conditions for making effervescent compressed forms (for example, less than about 25 C and less than 20% relative humidity) using either a Korsch, Carver or Kilian press. The amounts of materials used are on a weight percent of weight of the tablet formed, as set out in Table 1. The materials were used "as is" basis as received from the supplier. The materials used are described in Table 2.

TABLE 1

| Component | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Sodium carbonate | 50.00% | 50.00% | 30.00% | | | | 19.50% | 21.00% | 20.70% | 21.00% |
| Sodium bicarbonate | 30.00% | 29.00% | 40.00% | 70.00% | 70.00% | 70.00% | 50.00% | 50.00% | 50.00% | 50.00% |
| Citric acid | 20.00% | 19.00% | 27.70% | 26.50% | 25.50% | 24.50% | 25.00% | 25.00% | 25.00% | 25.00% |
| Glucopon 50 G | | | | 2.00% | 2.00% | 2.00% | 2.00% | 2.00% | 2.00% | 2.00% |
| Acusol 771 | | | | 0.50% | 1.00% | 1.50% | 1.50% | | | |
| Polyplasdone XL | | 2.00% | 2.00% | 1.00% | 1.50% | 2.00% | 2.00% | 2.00% | 2.00% | |
| Avicel BK 200 | | | | | | | | | | 2.00% |
| Fragrance | | | 0.30% | | | | | | 0.30% | |
| TOTAL | 100.00% | 100.00% | 100.00% | 100.00% | 100.00% | 100.00% | 100.00% | 100.00% | 100.00% | 100.00% |
| Tablet Size (gram) | 20 | 20 | 20 | 20 | 20 | 20 | 20 | 20 | 20 | 20 |

| Component | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| Sodium carbonate | 22.00% | 20.69% | 20.85% | 13.50% | 17.84% | 13.35% | 17.69% | 6.85% | 11.19% | 12.35% |
| Sodium bicarbonate | 50.00% | 50.00% | 50.00% | 50.00% | 50.00% | 50.00% | 50.00% | 50.00% | 50.00% | 50.00% |
| Citric acid | 25.00% | 25.00% | 25.00% | 25.00% | 25.00% | 25.00% | 25.00% | 25.00% | 25.00% | 25.00% |
| BTC 824 P-100 | | | | | 3.16% | | 3.16% | | 3.16% | |
| BTC 2125 M P-40 | | | | 7.50% | | 7.50% | | 7.50% | | 7.50% |
| BTC 8358 | | 0.31% | | | | | | | | |
| Glucopon 50 G | 2.00% | 2.00% | 2.00% | 2.00% | 2.00% | 2.00% | 2.00% | 2.00% | 2.00% | 2.00% |
| Polyplasdone XL | 1.00% | 2.00% | 2.00% | 2.00% | 2.00% | 2.00% | 2.00% | 1.50% | 1.50% | 3.00% |
| Avicel BK 200 | | | | | | | | 7.00% | 7.00% | |
| Fragrance | | | 0.15% | | | 0.15% | 0.15% | 0.15% | 0.15% | 0.15% |
| TOTAL | 100.00% | 100.00% | 100.00% | 100.00% | 100.00% | 100.00% | 100.00% | 100.00% | 100.00% | 100.00% |
| Tablet Size (gram) | 20 | 20 | 20 | 35 | 35 | 35 | 35 | 35 | 35 | 35 |

| Component | Ex. 21 | Ex. 22 | Ex. 23 | Ex. 24 | Ex. 25 | Ex. 26 | Ex. 27 | Ex. 28 | Ex. 29 | Ex. 30 |
|---|---|---|---|---|---|---|---|---|---|---|
| Sodium carbonate | 16.69% | 19.85% | 13.10% | 17.44% | 11.10% | 15.44% | 28.35% | 32.69% | 8.35% | 12.69% |
| Sodium metasilicate | | | | | | | | | 5.00% | 5.00% |
| Sodium bicarbonate | 50.00% | 50.00% | 50.00% | 50.00% | 50.00% | 50.00% | 50.00% | 50.00% | 50.00% | 50.00% |
| Citric acid | 25.00% | 25.00% | 25.00% | 25.00% | 25.00% | 25.00% | 10.00% | 10.00% | 25.00% | 25.00% |
| BTC 824 P-100 | 3.16% | | | 3.16% | | 3.16% | | 3.16% | | 3.16% |
| BTC 2125 M P-40 | | | 7.50% | | 7.50% | | 7.50% | | 7.50% | |
| Glucopon 50 G | 2.00% | 2.00% | | | 2.00% | 2.00% | 2.00% | 2.00% | 2.00% | 2.00% |
| Polyplasdone XL | 3.00% | 3.00% | 3.00% | 3.00% | 3.00% | 3.00% | 2.00% | 2.00% | 2.00% | 2.00% |
| Acusol 445 ND | | | 1.25% | 1.25% | 1.25% | 1.25% | | | | |
| Fragrance | 0.15% | 0.15% | 0.15% | 0.15% | 0.15% | 0.15% | 0.15% | 0.15% | 0.15% | 0.15% |
| TOTAL | 100.00% | 100.00% | 100.00% | 100.00% | 100.00% | 100.00% | 100.00% | 100.00% | 100.00% | 100.00% |
| Tablet Size (gram) | 35 | 35 | 35 | 35 | 35 | 35 | 35 | 35 | 35 | 35 |

| Component | Ex. 31 | Ex. 32 | Ex. 33 | Ex. 34 | Ex. 35 | Ex. 36 | Ex. 37 | Ex. 38 | Ex. 39 | Ex. 40 |
|---|---|---|---|---|---|---|---|---|---|---|
| Sodium carbonate | 22.69% | | 18.27% | 19.85% | 18.27% | 19.85% | 17.09% | 18.35% | 16.18% | 18.88% |
| Sodium metasilicate | | 17.69% | | | | | | | | |
| Sodium bicarbonate | 35.00% | 50.00% | 50.00% | 50.00% | 50.00% | 50.00% | 50.00% | 50.00% | 50.00% | 50.00% |
| Citric acid | 35.00% | 25.00% | 25.00% | 25.00% | 25.00% | 25.00% | 25.00% | 25.00% | 25.00% | 25.00% |
| BTC 824 P-100 | 3.16% | 3.16% | 1.58% | | 1.58% | | 2.77% | 1.58% | | 1.05% |
| BTC 2125 M P-40 | | | | | | | | | 3.75% | |
| Glucopon 50 G | 2.00% | 2.00% | 2.00% | 2.00% | 2.00% | 2.00% | 2.00% | 2.00% | 2.00% | 2.00% |
| Arbocel TF 30 HG | | | 3.00% | 3.00% | | | 3.00% | 3.00% | 3.00% | 3.00% |
| Polyplasdone XL | 2.00% | 2.00% | | | 3.00% | 3.00% | | | | |
| Fragrance | 0.15% | 0.15% | 0.15% | 0.15% | 0.15% | 0.15% | 0.15% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 35 | 35 | 35 | 35 | 35 | 35 | 20 | 35 | 35 | 35 |

TABLE 1-continued

| Component | Ex. 41 | Ex. 42 | Ex. 43 | Ex. 44 | Ex. 45 | Ex. 46 | Ex. 47 | Ex. 48 | Ex. 49 | Ex. 50 |
|---|---|---|---|---|---|---|---|---|---|---|
| Sodium carbonate | 17.35% | 17.88% | 16.88% | 15.88% | | | | | | |
| STPP hexahydrate | | | | | | | | | 12.00% | 12.00% |
| Sodium citrate dihydrate | | | | | | | 14.16% | | 6.16% | 5.16% |
| Sodium bicarbonate | 50.00% | 50.00% | 50.00% | 50.00% | 64.16% | 59.44% | 50.00% | 66.87% | 50.00% | 50.00% |
| Citric acid | 25.00% | 25.00% | 25.00% | 25.00% | 25.00% | 29.72% | 25.00% | 22.29% | 25.00% | 25.00% |
| BTC 824 P-100 | 1.58% | 1.05% | 1.05% | 1.05% | 2.77% | 2.77% | 2.77% | 2.77% | 2.77% | 2.77% |
| Glucopon 50 G | 2.00% | 2.00% | 2.00% | 2.00% | 2.00% | 2.00% | 2.00% | 2.00% | 2.00% | 2.00% |
| Arbocel TF 30 HG | 4.00% | 4.00% | 5.00% | 6.00% | 6.00% | 6.00% | 6.00% | 6.00% | 2.00% | 3.00% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 35 | 35 | 35 | 35 | 20 | 20 | 20 | 20 | 20 | 20 |

| Component | Ex. 51 | Ex. 52 | Ex. 53 | Ex. 54 | Ex. 55 | Ex. 56 | Ex. 57 | Ex. 58 | Ex. 59 | Ex. 60 |
|---|---|---|---|---|---|---|---|---|---|---|
| STPP hexahydrate | 5.00% | 5.00% | | | | | | | | |
| Sodium citrate dihydrate | 13.16% | 12.16% | | | | | | | | |
| Sodium bicarbonate | 50.00% | 50.00% | 65.11% | 68.37% | 60.44% | 68.30% | 60.71% | 68.59% | 67.85% | 67.85% |
| Citric acid | 25.00% | 25.00% | 26.05% | 22.79% | 30.22% | 22.77% | 30.35% | 22.86% | 22.61% | 22.61% |
| BTC 824 P-100 | 2.77% | 2.77% | 2.77% | 2.77% | 2.77% | 2.77% | 2.77% | 2.37% | 2.37% | 2.37% |
| Valfor 100 | | | | | 0.50% | 0.10% | 0.10% | 0.10% | 0.10% | 0.10% |
| Glucopon 50 G | 2.00% | 2.00% | 2.00% | 2.00% | 2.00% | 2.00% | 2.00% | 2.00% | 2.00% | 2.00% |
| PEG 6000 | | | | | | | | | 1.00% | 2.00% |
| Acusol 771 | 2.00% | 1.50% | | | | | | | | |
| Arbocel TF 30 HG | | 1.50% | 4.00% | 4.00% | 4.00% | 4.00% | 4.00% | 4.00% | 4.00% | 3.00% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 20 | 20 | 20 | 20 | 20 | 20 | 20 | 20 | 20 | 20 |

| Component | Ex. 61 | Ex. 62 | Ex. 63 | Ex. 64 | Ex. 65 | Ex. 66 | Ex. 67 | Ex. 68 | Ex. 69 | Ex. 70 |
|---|---|---|---|---|---|---|---|---|---|---|
| Sodium bicarbonate | 67.10% | 67.19% | 68.13% | 68.69% | 69.81% | 66.44% | 67.56% | 37.00% | 50.00% | 37.70% |
| Citric acid | 22.36% | 22.39% | 22.70% | 22.89% | 23.27% | 22.14% | 22.52% | 8.00% | 25.00% | 8.00% |
| Trisodium citrate dihydrate | | | | | | | | 30.00% | | 30.00% |
| Sodium carbonate | | | | | | | | 10.42% | 15.05% | 10.42% |
| BTC 824 P-100 | 2.37% | | | | | | | | | |
| Barquat MS-100 | | 2.25% | 2.25% | 2.25% | 2.25% | 2.25% | 2.25% | 2.50% | 1.80% | 1.80% |
| Valfor 100 | 0.10% | 0.10% | 0.10% | 0.10% | 0.10% | 0.10% | 0.10% | | | |
| Glucopon 50 G | 2.00% | 2.00% | 1.25% | 2.00% | 0.50% | 2.00% | 0.50% | 2.00% | 2.00% | 2.00% |
| Avicel BK 200 | | | | | | | | 3.00% | | 3.00% |
| Arbocel TF 0406 | | | | | | | | 3.00% | 3.00% | 3.00% |
| Arbocel TF 30 HG | 4.00% | 4.00% | 4.50% | 3.00% | 3.00% | 6.00% | 6.00% | | | |
| Optigel SH | | | | | | | | 0.93% | | 0.93% |
| PEG 6000 | 2.00% | 2.00% | 1.00% | 1.00% | 1.00% | 1.00% | 1.00% | 3.00% | 3.00% | 3.00% |
| Sipernat 22 | | | | | | | | 0.08% | 0.08% | 0.08% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 20 | 20 | 20 | 20 | 20 | 20 | 20 | 18 | 25 | 25 |

| Component | Ex. 71 | Ex. 72 | Ex. 73 | Ex. 74 | Ex. 75 | Ex. 76 | Ex. 77 | Ex. 78 | Ex. 79 | Ex. 80 |
|---|---|---|---|---|---|---|---|---|---|---|
| Sodium bicarbonate | 39.50% | 40.05% | 39.53% | 58.54% | 37.00% | 49.05% | 50.54% | 50.54% | 50.54% | 42.00% |
| Citric acid | 8.00% | 8.00% | 39.53% | 19.51% | | | 38.51% | 38.51% | 38.51% | 32.00% |
| Trisodium citrate dihydrate | 30.00% | 30.00% | | | 38.00% | 38.00% | | | | |
| Sodium carbonate (course) | 10.42% | | 10.00% | 10.00% | 10.43% | | | | | |
| Sodium carbonate (fine) | | | | | | | | | | 5.00% |
| Barquat MS-100 | | 1.80% | 1.80% | 1.80% | 2.50% | 1.80% | 1.80% | 1.80% | | 1.80% |
| Prismalac 40 | | | | | | | | | | 11.05% |
| Glucopon 50 G | 2.00% | 2.00% | 2.00% | 2.00% | 2.00% | 2.00% | 2.00% | 2.00% | 2.00% | 2.00% |
| Avicel BK 200 | 3.00% | | | | 3.00% | 3.00% | | | | |
| Avicel NT 050 | | | | | | | | | | 2.00% |
| Arbocel TF 0406 | 3.00% | | 2.00% | 3.00% | 3.00% | 3.00% | 4.00% | 4.00% | 4.00% | |
| Optigel SH | 0.93% | | | 2.00% | 0.93% | | | | | |
| Kyrosan E18 | | 15.00% | 2.00% | | | | | | | |
| PEG 6000 | 3.00% | 3.00% | 3.00% | 3.00% | 3.00% | 3.00% | 3.00% | 3.00% | 3.00% | 3.00% |
| PEG 4000 | | | | | | | | | | 1.00% |
| Sipernat 22 | 0.08% | 0.08% | 0.08% | 0.08% | 0.08% | 0.08% | 0.08% | 0.08% | 0.08% | 0.08% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 98.20% | 100.00% |
| Tablet Size (gram) | 25 | 25 | 25 | 25 | 25 | 25 | 25 | 25 | 25 | 25 |

TABLE 1-continued

| Component | Ex. 81 | Ex. 82 | Ex. 83 | Ex. 84 | Ex. 85 | Ex. 86 | Ex. 87 | Ex. 88 | Ex. 89 | Ex. 90 |
|---|---|---|---|---|---|---|---|---|---|---|
| Sodium bicarbonate | 28.38% | 36.92% | 28.38% | 28.38% | 28.38% | 28.38% | 28.38% | 28.38% | 33.51% | 21.00% |
| Citric acid | 21.62% | 28.13% | 21.62% | 21.62% | 21.62% | 21.62% | 21.62% | 21.62% | 25.54% | 16.00% |
| Trisodium citrate dihydrate | | | 15.00% | 20.00% | | | | 10.00% | | |
| Sodium carbonate (fine) | 5.00% | 5.00% | 5.00% | 5.00% | 5.00% | 15.00% | 15.00% | 15.00% | 10.00% | |
| Sodium carbonate (course) | | | | 5.00% | | | | | | 10.00% |
| Sodium Sulfate | | | | | 1.50% | | | | | |
| Barquat MS-100 | 1.80% | 1.80% | 1.80% | 1.80% | 1.80% | 1.80% | 1.80% | 1.80% | 1.80% | 4.50% |
| Prismalac 40 | 35.05% | 20.00% | | | | | | | 10.00% | 22.35% |
| Karion | | | 22.05% | 12.05% | 35.05% | 27.05% | 17.05% | 27.05% | 15.00% | 20.00% |
| Glucopon 50 G | 2.00% | 2.00% | 2.00% | 2.00% | 2.00% | 2.00% | 2.00% | | | |
| Pluronic F68 (ground) | | | | | | | | | | 2.00% |
| Avicel NT. 050 | | | | | | | | 2.00% | | |
| Sodium alginate | 2.00% | 2.00% | | | | | | | | |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.50% | 1.00% | 1.00% | 1.00% | 1.00% | |
| PEG 1450 | | | | | | | | | | 1.00% |
| Sipernat 22 | 0.08% | 0.08% | 0.08% | 0.08% | 0.08% | 0.08% | 0.08% | 0.08% | 0.08% | 0.08% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 25 | 25 | 25 | 25 | 25 | 25 | 25 | 25 | 25 | 10 |

| Component | Ex. 91 | Ex. 92 | Ex. 93 | Ex. 94 | Ex. 95 | Ex. 96 | Ex. 97 | Ex. 98 | Ex. 99 | Ex. 100 |
|---|---|---|---|---|---|---|---|---|---|---|
| Sodium bicarbonate | 21.00% | 21.00% | 21.00% | 33.51% | 28.38% | 28.38% | 28.38% | 33.96% | 41.52% | 33.96% |
| Citric acid | 16.00% | 16.00% | 16.00% | 25.54% | 21.62% | 21.62% | 21.62% | 25.88% | 31.64% | 25.88% |
| Sodium carbonate (fine) | 10.00% | 10.00% | 10.00% | 5.00% | 10.00% | 10.00% | 10.00% | 10.00% | 10.00% | 10.00% |
| STPP | | | | | | 15.00% | | | | |
| Barquat MS-100 | 4.50% | 4.50% | 4.50% | | 4.50% | 4.50% | 4.50% | 4.50% | 4.50% | 4.50% |
| Prismalac 40 | 22.35% | 20.35% | 20.35% | 15.00% | 14.00% | 6.35% | 16.00% | | 6.19% | 19.51% |
| Karion | 20.00% | 20.00% | 20.00% | 14.80% | 13.85% | 6.00% | 15.35% | 19.51% | | |
| Pluronic F68 (ground) | 2.00% | 2.00% | 2.00% | 2.00% | 2.00% | 2.00% | | 2.00% | 2.00% | 2.00% |
| Acusol 771 | | | | | | | 2.00% | | | |
| Hexylcellosolve on microsponge | | | | | 1.50% | | | | | |
| Avicel NT 050 | | 2.00% | | | | | | | | |
| Arbocel TF 30 HG | | | 2.00% | | | | | | | |
| PEG 6000 | 3.00% | 3.00% | 3.00% | 3.00% | 3.00% | 3.00% | 3.00% | 3.00% | 3.00% | 3.00% |
| PEG 1450 | 1.00% | 1.00% | 1.00% | 1.00% | 1.00% | 1.00% | 1.00% | 1.00% | 1.00% | 1.00% |
| Sipernat 22 | 0.08% | 0.08% | 0.08% | 0.08% | 0.08% | 0.08% | 0.08% | 0.08% | 0.08% | 0.08% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.00% | 100.00% |
| Tablet Size (gram) | 10 | 10 | 10 | 10 | 10 | 10 | 10 | 10 | 10 | 10 |

| Component | Ex. 101 | Ex. 102 | Ex. 103 | Ex. 104 | Ex. 105 | Ex. 106 | Ex. 107 | Ex. 108 | Ex. 109 | Ex. 110 |
|---|---|---|---|---|---|---|---|---|---|---|
| Sodium bicarbonate | 41.52% | 37.96% | 27.68% | 34.18% | 34.18% | 31.04% | 37.96% | 34.39% | 27.68% | 31.04% |
| Citric acid | 31.64% | 28.92% | 21.09% | 26.04% | 26.04% | 23.65% | 28.92% | 26.20% | 21.09% | 23.65% |
| Sodium carbonate (fine) | 10.00% | 10.00% | 10.00% | 10.00% | 10.00% | 10.00% | 10.00% | 10.00% | 10.00% | 10.00% |
| Barquat MS-100 | 4.50% | 4.50% | 4.50% | 4.50% | 4.50% | 4.50% | 4.50% | 4.50% | 4.50% | 4.50% |
| Prismalac 40 | | 4.69% | 19.51% | 4.69% | 14.44% | 10.22% | 7.78% | 9.38% | 11.09% | 14.44% |
| Karion | 6.19% | 7.78% | 11.07% | 14.44% | 4.69% | 14.44% | 4.69% | 9.38% | 19.51% | 10.22% |
| Pluronic F68 (ground) | 2.00% | 2.00% | 2.00% | 2.00% | 2.00% | 2.00% | 2.00% | 2.00% | 2.00% | 2.00% |
| PEG 6000 | 3.00% | 3.00% | 3.00% | 3.00% | 3.00% | 3.00% | 3.00% | 3.00% | 3.00% | 3.00% |
| PEG 1450 | 1.00% | 1.00% | 1.00% | 1.00% | 1.00% | 1.00% | 1.00% | 1.00% | 1.00% | 1.00% |
| Sipernat 22 | 0.08% | 0.08% | 0.08% | 0.08% | 0.08% | 0.08% | 0.08% | 0.08% | 0.08% | 0.08% |
| Fragrance | 0.08% | 0.08% | 0.08% | 0.08% | 0.08% | 0.08% | 0.08% | 0.08% | 0.08% | 0.08% |
| TOTAL | 100.00% | 100.00% | 100.00% | 100.00% | 100.00% | 100.00% | 100.00% | 100.00% | 100.02% | 100.00% |
| Tablet Size (gram) | 10 | 10 | 10 | 10 | 10 | 10 | 10 | 10 | 10 | 10 |

| Component | Ex. 111 | Ex. 112 | Ex. 113 | Ex. 114 | Ex. 115 | Ex. 116 | Ex. 117 | Ex. 118 | Ex. 119 | Ex. 120 |
|---|---|---|---|---|---|---|---|---|---|---|
| Sodium bicarbonate | 28.38% | 28.38% | 28.38% | 28.38% | 28.38% | 28.38% | 28.38% | 34.39% | 39.73% | 41.24% |
| Citric acid | 21.62% | 21.62% | 21.62% | 21.62% | 21.62% | 21.62% | 21.62% | 30.27% | 30.27% | 30.76% |
| Sodium carbonate (fine) | 10.00% | 10.00% | 10.00% | 10.00% | 10.00% | 10.00% | 10.00% | 10.00% | 10.00% | 10.00% |
| Barquat MS-100 | 4.50% | 4.50% | 4.50% | 4.50% | 9.00% | 9.00% | | 9.00% | 4.50% | 4.50% |
| Vantocil 100 | | | | | | | 4.50% | | | |
| Prismalac 40 | 14.20% | 13.20% | | 13.95% | 10.70% | 11.20% | 13.45% | | 3.45% | 3.45% |
| Karion | 14.00% | 13.00% | 27.90% | 13.95% | 10.70% | 11.20% | 13.45% | 2.40% | 3.45% | 3.45% |
| Pluronic F68 (ground) | | 2.00% | | | 2.00% | | | | | |
| Hexylcellosolve on microsponge | 3.00% | 3.00% | 3.00% | 3.00% | 3.00% | 2.00% | 2.00% | 2.00% | 2.00% | 2.00% |
| PEG 6000 | 3.00% | 3.00% | 3.00% | 3.00% | 3.00% | 3.00% | 3.00% | 3.00% | 3.00% | 3.00% |

TABLE 1-continued

| Component | Ex. 121 | Ex. 122 | Ex. 123 | Ex. 124 | Ex. 125 | Ex. 126 | Ex. 127 | Ex. 128 | Ex. 129 | Ex. 130 |
|---|---|---|---|---|---|---|---|---|---|---|
| PEG 1500 | | | 1.00% | 1.00% | 1.00% | 1.00% | 1.00% | 1.00% | 1.00% | 1.00% |
| PEG 1450 | 1.00% | 1.00% | | | | | | | | |
| Fragrance on carrier | 0.30% | 0.30% | 0.60% | 0.60% | 0.60% | 0.60% | 0.60% | 0.60% | 0.60% | 0.60% |
| TOTAL | 100.00% | 100.00% | 100.00% | 100.00% | 100.00% | 100.00% | 100.00% | 94.66% | 100.00% | 100.00% |
| Tablet Size (gram) | 10 | 10 | 10 | 10 | 10 | 10 | 10 | 10 | 10 | 10 |

| Component | Ex. 121 | Ex. 122 | Ex. 123 | Ex. 124 | Ex. 125 | Ex. 126 | Ex. 127 | Ex. 128 | Ex. 129 | Ex. 130 |
|---|---|---|---|---|---|---|---|---|---|---|
| Sodium bicarbonate | 46.24% | 45.24% | 45.24% | 46.24% | 46.24% | 45.75% | 41.75% | 41.75% | 38.80% | 50.00% |
| Citric acid | 30.76% | 30.76% | 30.76% | 30.76% | 30.76% | 33.25% | 30.25% | 30.25% | 28.20% | 25.00% |
| Sodium carbonate (fine) | 5.00% | 5.00% | 5.00% | 5.00% | 5.00% | 5.00% | 5.00% | 5.00% | 10.00% | 5.00% |
| Barquat MS-100 | 4.50% | 4.50% | 4.50% | 3.50% | 4.50% | 4.50% | 9.00% | 9.00% | 9.00% | 6.00% |
| Prismalac 40 | 3.45% | | 7.90% | 3.45% | 3.45% | 3.45% | 3.50% | 3.50% | 3.50% | 3.50% |
| Karion | 3.45% | 7.90% | | 3.45% | 3.45% | 3.45% | 3.50% | 3.50% | 3.50% | 3.50% |
| Pluronic F68 (ground) | 2.00% | 2.00% | 2.00% | 2.00% | 2.00% | | 2.00% | 2.00% | 2.00% | 2.00% |
| Hexylcellosolve on microsponge | | | | | | | | 0.50% | | |
| Microsponge | | | | | | | | 0.50% | 0.50% | 0.50% |
| PEG 6000 | 3.00% | 3.00% | 3.00% | 3.00% | | | 3.00% | 3.00% | 3.00% | 3.00% |
| PEG 4000 | | | | | 1.00% | 1.00% | 1.00% | 1.00% | 1.00% | 1.00% |
| PEG 1500 | 1.00% | 1.00% | 1.00% | 2.00% | | | | | | |
| Fragrance on carrier | 0.60% | 0.60% | 0.60% | 0.60% | 0.60% | 0.60% | 0.50% | 0.50% | 0.50% | 0.50% |
| TOTAL | 100.00% | 100.00% | 100.00% | 100.00% | 100.00% | 100.00% | 100.000% | 100.00% | 100.00% | 100.00% |
| Tablet Size (gram) | 10 | 10 | 10 | 12.86 | 10 | 10 | 10 | 10 | 10 | 15 |

| Component | Ex. 131 | Ex. 132 | Ex. 133 | Ex. 134 | Ex. 135 | Ex. 136 | Ex. 137 | Ex. 138 | Ex. 139 | Ex. 140 |
|---|---|---|---|---|---|---|---|---|---|---|
| Sodium bicarbonate | 39.00% | 39.15% | 38.95% | 50.00% | 50.00% | 45.00% | 45.00% | 50.00% | 34.65% | 50.00% |
| Citric acid | 29.00% | 28.35% | 28.20% | 23.75% | 23.65% | 22.15% | 20.15% | 21.75% | 17.30% | 21.75% |
| Sodium carbonate (fine) | 10.00% | 10.00% | 10.00% | 5.00% | 5.00% | 10.00% | 10.00% | 5.00% | 10.00% | 5.00% |
| Barquat MS-100 | 9.00% | 9.00% | 9.00% | 7.50% | 7.50% | 9.00% | 9.00% | 7.50% | 26.30% | 7.50% |
| Prismalac 40 | 3.50% | 3.50% | 3.50% | 3.50% | 3.50% | 3.50% | 3.50% | 3.50% | 3.50% | 3.50% |
| Karion | 3.50% | 3.50% | 3.50% | 3.50% | 3.50% | 3.50% | 3.50% | 3.50% | | 3.50% |
| Pluronic F68 (ground) | 2.00% | 2.00% | 2.00% | 2.00% | 2.00% | 2.00% | 2.00% | 2.00% | 2.00% | |
| Empilan KM 50-PW | | | | | | | | | | 2.00% |
| Microsponge | 0.50% | 0.50% | 0.50% | 0.50% | 0.50% | 0.50% | 0.50% | 0.50% | 2.00% | 0.50% |
| PEG 6000 | 3.00% | 3.00% | 3.00% | 3.00% | 3.00% | 3.00% | 3.00% | 3.00% | 3.00% | 3.00% |
| PEG 4000 | | 0.50% | 1.00% | 1.00% | 1.00% | 1.00% | 1.00% | 1.00% | 1.00% | 1.00% |
| Magnesium stearate | | | 0.10% | | 0.10% | 0.10% | 0.10% | | | |
| Fragrance on carrier | 0.50% | 0.50% | 0.25% | 0.25% | 0.25% | 0.25% | 0.25% | 0.25% | 0.25% | 0.25% |
| Blue speckles | | | | | | | | 2.00% | 2.00% | 2.00% |
| TOTAL | 100.00% | 100.00% | 100.00% | 100.00% | 100.00% | 100.00% | 100.00% | 100.00% | 100.00% | 100.00% |
| Tablet Size (gram) | 10 | 10 | 10 | 12 | 12 | 10 | 10 | 12 | 12 | 12 |

| Component | Ex. 141 | Ex. 142 | Ex. 143 | Ex. 144 | Ex. 145 | Ex. 146 | Ex. 147 | Ex. 148 | Ex. 149 | Ex. 150 |
|---|---|---|---|---|---|---|---|---|---|---|
| Sodium bicarbonate | 35.00% | 50.00% | 50.00% | 50.00% | 46.00% | 46.50% | 46.50% | 43.25% | 46.00% | 46.40% |
| Citric acid | 17.45% | 23.75% | 21.25% | 21.25% | 21.75% | 21.75% | 21.75% | 20.00% | 21.75% | 21.75% |
| Sodium carbonate (fine) | 5.00% | 5.00% | 5.00% | 5.00% | 5.00% | 5.00% | 5.00% | 5.00% | 5.00% | 5.00% |
| Barquat MS-100 | 26.30% | 7.50% | 7.50% | 7.50% | 7.50% | 7.50% | 7.50% | 7.50% | 7.50% | 7.50% |
| Vantocil 100 | | | | | | | | | | |
| Prismalac 40 | 3.50% | | 3.50% | 3.50% | 3.50% | 3.50% | 3.50% | 3.50% | 3.50% | 3.50% |
| Karion | 3.50% | 5.00% | 3.50% | 3.50% | 3.50% | 3.50% | 3.50% | 3.50% | 3.50% | 3.50% |
| Pluronic F68 | 2.00% | | 2.00% | 2.00% | 2.00% | 2.00% | 2.00% | 2.00% | 2.00% | 2.00% |
| Empilan KM 50-PW | | 2.00% | | | | | | | | |
| Microsponge | 1.00% | 0.50% | 0.50% | 0.50% | | 0.50% | | 0.50% | 0.50% | |
| Hysorb P 7050 | | | | | | | | 0.50% | | 0.10% |
| Sokolan CP5 | | | | | 0.50% | | | | | |
| Avicel NT 050 | | | | 0.50% | 1.00% | 0.50% | 0.50% | 0.50% | 1.00% | 1.00% |
| Arbocel TF 30 HG | | | 0.50% | | | | | | | |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| Blue speckles | 2.00% | 2.00% | 2.00% | 2.00% | 5.00% | 5.00% | 5.00% | 10.00% | 5.00% | 5.00% |
| TOTAL | 100.00% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 12 | 12 | 12 | 12 |

| Component | Ex. 151 | Ex. 152 | Ex. 153 | Ex. 154 | Ex. 155 | Ex. 156 | Ex. 157 | Ex. 158 | Ex. 159 | Ex. 160 |
|---|---|---|---|---|---|---|---|---|---|---|
| Sodium bicarbonate | 46.40% | 46.25% | 45.75% | 46.25% | 46.25% | 44.25% | 48.00% | 47.00% | 47.00% | 47.00% |
| Citric acid | 21.75% | 21.75% | 21.75% | 21.75% | 21.75% | 21.75% | 20.00% | 20.50% | 20.00% | 20.00% |
| Sodium carbonate (fine) | 5.00% | 5.00% | 5.00% | 5.00% | 5.00% | 5.00% | 5.00% | 5.00% | 5.00% | 5.00% |
| Barquat MS-100 | 7.50% | 7.50% | 7.50% | 7.50% | 7.50% | 7.50% | 7.50% | 7.50% | 7.50% | 7.50% |
| Prismalac 40 | 3.50% | 3.50% | 3.50% | 3.50% | 3.50% | 3.50% | 3.50% | 3.50% | 3.50% | 3.50% |
| Karion | 3.50% | 3.50% | 3.50% | 3.50% | 3.50% | 3.50% | 3.50% | 3.50% | 3.50% | 3.50% |

TABLE 1-continued

| Component | | | | | | | | | | |
|---|---|---|---|---|---|---|---|---|---|---|
| Pluronic F68 | 2.00% | 2.00% | 2.00% | | | | | | | |
| Pluronic F38 | | | | 2.00% | | 2.00% | | 2.00% | 2.00% | |
| Empilan KM 50-PW | | | | | 2.00% | 2.00% | 2.00% | | | 2.00% |
| Hysorb P 7050 | 0.25% | 0.25% | 0.25% | 0.25% | 0.25% | 0.25% | 0.25% | 0.25% | 0.25% | 0.25% |
| Sokolan CP5 | | | 0.50% | | | | | | | |
| Avicel NT 050 | 1.00% | | | 1.00% | 1.00% | 1.00% | 1.00% | 1.50% | 2.00% | 2.00% |
| Sorb-Sol | | | 1.00% | | | | | | | |
| Sorb-Cel | | 1.00% | | | | | | | | |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| Blue speckles | 5.00% | 5.00% | 5.00% | 5.00% | 5.00% | 5.00% | 5.00% | 5.00% | 5.00% | 5.00% |
| TOTAL | 100.15% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 12 | 12 | 12 | 12 |

| Component | Ex. 161 | Ex. 162 | Ex. 163 | Ex. 164 | Ex. 165 | Ex. 166 | Ex. 167 | Ex. 168 | Ex. 169 | Ex. 170 |
|---|---|---|---|---|---|---|---|---|---|---|
| Sodium bicarbonate | 48.00% | 64.00% | 49.00% | 40.00% | 51.00% | 40.00% | 40.00% | 40.00% | 48.17% | 56.50% |
| Citric acid | 20.00% | 15.00% | 30.00% | 15.00% | 30.00% | 15.00% | 30.00% | 15.00% | 22.50% | 22.50% |
| Sodium carbonate (fine) | 5.00% | 5.00% | 5.00% | 5.00% | 5.00% | 5.00% | 5.00% | 5.00% | 5.00% | 5.00% |
| Barquat MS-100 | 7.50% | 7.50% | 7.50% | 7.50% | 7.50% | 7.50% | 7.50% | 7.50% | 7.50% | 7.50% |
| Prismalac 40 | 3.50% | | | 10.50% | | 12.00% | 4.50% | 14.00% | 4.09% | |
| Karion | 3.50% | | | 10.50% | | 12.00% | 4.50% | 14.00% | 4.09% | |
| Pluronic F68 | 2.00% | 4.00% | | | | | | | 1.33% | |
| Pluronic F38 | | | 2.00% | | | 4.00% | | | 1.33% | 4.00% |
| Empilan KM 50-PW | | | 2.00% | 4.00% | 2.00% | | 4.00% | | | |
| Hysorb P 7050 | 0.25% | 0.25% | 0.25% | 0.25% | 0.25% | 0.25% | 0.25% | 0.25% | 0.25% | 0.25% |
| Avicel NT 050 | 1.00% | | | 3.00% | | | | | 1.50% | |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| Blue speckles | 5.00% | | | | | | | | | |
| TOTAL | 100.00% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 12 | 12 | 12 | 12 |

| Component | Ex. 171 | Ex. 172 | Ex. 173 | Ex. 174 | Ex. 175 | Ex. 176 | Ex. 177 | Ex. 178 | Ex. 179 | Ex. 180 |
|---|---|---|---|---|---|---|---|---|---|---|
| Sodium bicarbonate | 40.00% | 40.00% | 54.00% | 40.00% | 48.00% | 40.00% | 54.50% | 40.00% | 61.00% | 64.00% |
| Citric acid | 15.00% | 22.50% | 15.00% | 30.00% | 30.00% | 22.50% | 18.75% | 15.00% | 15.00% | 15.00% |
| Sodium carbonate (fine) | 5.00% | 5.00% | 5.00% | 5.00% | 5.00% | 5.00% | 5.00% | 5.00% | 5.00% | 5.00% |
| Barquat MS-100 | 7.50% | 7.50% | 7.50% | 7.50% | 7.50% | 7.50% | 7.50% | 7.50% | 7.50% | 7.50% |
| Prismalac 40 | 12.00% | 8.25% | 7.00% | 5.00% | | 8.00% | 2.00% | 11.25% | | |
| Karion | 12.00% | 8.25% | 7.00% | 5.00% | | 8.00% | 2.00% | 11.25% | | |
| Pluronic F68 | | 4.00% | | | 2.00% | 1.00% | 2.50% | 4.00% | 4.00% | |
| Pluronic F38 | | | | | | | 1.00% | 0.50% | | |
| Empilan KM 50-PW | 4.00% | | | | | 1.00% | 0.50% | | | 4.00% |
| Hysorb P 7050 | 0.25% | 0.25% | 0.25% | 0.25% | 0.25% | 0.25% | 0.25% | 0.25% | 0.25% | 0.25% |
| Avicel NT 050 | | | | 3.00% | 3.00% | 1.50% | 2.25% | 1.50% | 3.00% | |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| TOTAL | 100.00% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 12 | 12 | 12 | 12 |

| Component | Ex. 181 | Ex. 182 | Ex. 183 | Ex. 184 | Ex. 185 | Ex. 186 | Ex. 187 | Ex. 188 | Ex. 189 | Ex. 190 |
|---|---|---|---|---|---|---|---|---|---|---|
| Sodium bicarbonate | 40.00% | 61.00% | 40.00% | 61.00% | 49.00% | 63.00% | 51.50% | 40.00% | 49.00% | 63.00% |
| Citric acid | 30.00% | 15.00% | 30.00% | 15.00% | 30.00% | 15.00% | 30.00% | 15.00% | 30.00% | 15.00% |
| Sodium carbonate (fine) | 5.00% | 5.00% | 5.00% | 5.00% | 5.00% | 5.00% | 5.00% | 5.00% | 5.00% | 5.00% |
| Barquat MS-100 | 7.50% | 7.50% | 7.50% | 7.50% | 7.50% | 7.50% | 7.50% | 7.50% | 7.50% | 7.50% |
| Prismalac 40 | 5.50% | | 3.00% | | | | | 11.50% | | |
| Karion | 5.50% | | 3.00% | | | | | 11.50% | | |
| Pluronic F68 | | 4.00% | | | 2.00% | | | | | |
| Pluronic F38 | 2.00% | | 4.00% | 4.00% | | | | 2.00% | 2.00% | |
| Empilan KM 50-PW | | | | | 2.00% | 2.00% | | | | 2.00% |
| Hysorb P 7050 | 0.25% | 0.25% | 0.25% | 0.25% | 0.25% | 0.25% | 0.25% | 0.25% | 0.25% | 0.25% |
| Avicel NT 050 | | 3.00% | 3.00% | 3.00% | | 3.00% | 1.50% | 3.00% | | 3.00% |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| TOTAL | 100.00% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 12 | 12 | 12 | 12 |

TABLE 1-continued

| Component | Ex. 191 | Ex. 192 | Ex. 193 | Ex. 194 | Ex. 195 | Ex. 196 | Ex. 197 | Ex. 198 | Ex. 199 | Ex. 200 |
|---|---|---|---|---|---|---|---|---|---|---|
| Sodium bicarbonate | 43.00% | 40.00% | 68.00% | 40.00% | 40.00% | 45.00% | 43.00% | 40.00% | 42.50% | 40.00% |
| Citric add | 30.00% | 30.00% | 15.00% | 15.00% | 15.00% | 10.00% | 10.00% | 10.00% | 7.50% | 10.00% |
| Sodium carbonate (fine) | 5.00% | 5.00% | 5.00% | 5.00% | 5.00% | 5.00% | 5.00% | 10.00% | 10.00% | 10.00% |
| Barquat MS-100 | 7.50% | 7.50% | 7.50% | 7.50% | 7.50% | 7.50% | 7.50% | 7.50% | 7.50% | 7.50% |
| Prismalac 40 | 1.50% | 3.75% |  | 11.30% | 10.80% | 10.80% | 10.80% | 10.80% | 10.80% | 10.80% |
| Karion | 1.50% | 3.75% |  | 11.30% | 10.80% | 10.80% | 10.80% | 10.80% | 10.80% | 10.80% |
| Anhydrous STPP |  |  |  |  | 1.00% | 1.00% | 3.00% | 1.00% | 1.00% |  |
| Pluronic F68 |  | 4.00% |  | 1.02% | 1.02% | 1.02% | 1.02% | 1.02% | 1.02% | 1.02% |
| Pluronic F38 |  |  |  | 1.39% | 1.39% | 1.39% | 1.39% | 1.39% | 1.39% | 1.39% |
| Empilan KM 50-PW | 4.00% |  |  |  |  |  |  |  |  |  |
| Hysorb P 7050 | 0.25% | 0.25% | 0.25% | 0.25% | 0.25% | 0.25% | 0.25% | 0.25% | 0.25% | 0.25% |
| Avicel NT. 050 | 3.00% | 1.50% |  | 3.00% | 3.00% | 3.00% | 3.00% | 3.00% | 3.00% | 3.00% |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.25% | 0.25% | 0.25% | 0.25% | 0.25% | 0.25% |
| TOTAL | 100.00% | 100.00% | 100.00% | 100.00% | 100.00% | 100.00% | 100.00% | 100.00% | 100.00% | 99.00% |
| Tablet Size (gram) | 12 | 12 | 12 | 12 | 12 | 12 | 12 | 12 | 12 | 12 |

| Component | Ex. 201 | Ex. 202 | Ex. 203 | Ex. 204 | Ex. 205 | Ex. 206 | Ex. 207 | Ex. 208 | Ex. 209 | Ex. 210 |
|---|---|---|---|---|---|---|---|---|---|---|
| Sodium bicarbonate | 32.50% | 35.00% | 40.00% | 40.00% | 43.50% | 45.75% | 40.00% | 40.00% | 40.00% | 40.00% |
| Citric acid | 7.50% | 10.00% | 15.00% | 10.00% | 10.00% | 10.00% | 10.00% | 10.00% | 10.00% | 10.00% |
| Sodium carbonate (fine) | 20.00% | 15.00% | 5.00% | 10.00% | 10.00% | 10.00% | 10.00% | 10.00% | 10.00% | 10.00% |
| Barquat MS-100 | 7.50% | 7.50% | 7.50% | 7.50% | 3.75% | 1.50% | 1.80% | 1.80% | 1.80% | 1.80% |
| Prismalac 40 | 11.30% | 11.30% | 10.80% | 11.30% | 11.30% | 11.30% | 10.41% | 9.20% | 9.20% | 9.20% |
| Karion | 11.30% | 11.30% | 10.80% | 11.30% | 11.30% | 11.30% | 10.41% | 9.20% | 9.20% | 9.20% |
| NaOH (ground powder) |  |  |  | 1.00% |  |  |  |  |  |  |
| Pluronic F68 | 1.02% | 1.02% | 1.02% | 1.02% | 1.02% | 1.02% | 4.08% | 5.10% | 12.05% |  |
| Pluronic F38 | 1.39% | 1.39% | 1.39% | 1.39% | 1.39% | 1.39% | 5.56% | 6.95% |  | 12.05% |
| Hysorb P 7050 | 0.25% | 0.25% | 0.25% | 0.25% | 0.25% | 0.25% | 0.25% | 0.25% | 0.25% | 0.25% |
| Avicel NT 050 | 3.00% | 3.00% | 3.00% | 3.00% | 3.00% | 3.00% | 3.00% | 3.00% | 3.00% | 3.00% |
| PEG 6000 | 3.00% | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% | 1.00% |
| Fragrance on carrier | 0.25% | 0.25% | 0.25% | 0.25% | 0.50% | 0.50% | 0.50% | 0.50% | 0.50% | 0.50% |
| TOTAL | 100.00% | 100.00% | 100.00% | 100.00% | 100.00% | 100.00% | 100.00% | 100.00% | 100.00% | 100.00% |
| Tablet Size (gram) | 12 | 12 | 12 | 12 | 12 | 12 | 10 | 10 | 10 | 10 |

| Component | Ex. 211 | Ex. 212 | Ex. 213 | Ex. 214 | Ex. 215 | Ex. 216 | Ex. 217 | Ex. 218 | Ex. 219 |
|---|---|---|---|---|---|---|---|---|---|
| Sodium Bicarbonate (course) | 40.00% | 40.00% | 40.00% | 40.00% | 40.00% | 40.00% | 40.00% | 40.00% | 40.00% |
| Citric Acid | 10.00% | 10.00% | 10.00% | 10.00% |  |  |  |  |  |
| Citrocoat |  |  |  |  | 10.00% | 10.00% | 10.00% | 10.00% | 10.00% |
| Sodium Carbonate (light density) |  |  |  |  | 10.00% | 10.00% | 10.00% | 10.00% | 10.00% |
| Sodium Carbonate (fine) | 10.00% | 20.00% | 10.00% | 10.00% |  |  |  |  |  |
| Barquat MS-100 | 1.80% |  | 3.60% | 1.80% | 1.80% | 1.80% | 1.80% | 1.80% | 1.80% |
| Catigene T-50 |  | 6.00% |  |  |  |  |  |  |  |
| Prismalac 40 | 12.21% | 7.10% | 11.31% | 10.71% | 11.73% | 11.73% | 11.73% | 13.23% | 12.48% |
| Karion | 12.21% | 7.10% | 11.31% | 10.71% | 11.73% | 11.73% | 11.73% | 13.23% | 12.48% |
| Pluronic F68 | 2.55% | 1.80% | 2.55% | 2.55% |  |  |  |  |  |
| Pluronic F38 | 3.48% | 2.00% | 3.48% | 3.48% |  |  |  |  |  |
| Lutensol AT 25 |  |  |  |  |  | 6.00% |  |  |  |
| Lutensol AT 50 |  |  |  |  |  |  | 6.00% |  |  |
| Lutensol AT 80 |  |  |  |  |  |  |  | 6.00% | 3.00% | 4.50% |
| Hysorb P9070 |  |  |  |  | 0.25% | 0.25% | 0.25% | 0.25% | 0.25% |
| Hysrob P7050 | 0.25% | 0.25% | 0.25% | 0.25% |  |  |  |  |  |
| Avicel NT 050 | 3.00% | 1.25% | 3.00% | 6.00% | 4.00% | 4.00% | 4.00% | 4.00% | 4.00% |
| PEG 6000 | 3.00% | 3.00% | 3.00% | 3.00% | 3.00% | 3.00% | 3.00% | 3.00% | 3.00% |
| PEG 4000 | 1.00% | 1.00% | 1.00% | 1.00% | 1.00% | 1.00% | 1.00% | 1.00% | 1.00% |
| Fragrance on carrier | 0.50% | 0.50% | 0.50% | 0.50% |  |  |  |  |  |
| Fragrance |  |  |  |  | 0.50% | 0.50% | 0.50% | 0.50% | 0.50% |
| TOTAL | 100.00% | 100.00% | 100.00% | 100.00% | 100.00% | 100.00% | 100.00% | 100.00% | 100.00% |
| Tablet Size (gram) | 10 | 10 | 10 | 10 | 10 | 10 | 10 | 10 | 10 |

TABLE 2

| Component | Description |
|---|---|
| Avicel BK 200 | microcrystalline cellulose (FMC) |
| Avicel NT 050 | microcrystalline cellulose (FMC) |

TABLE 2-continued

| Component | Description |
|---|---|
| BTC 2125M-P40 | alkyl dimethyl ammonium chloride and alkyl dimethyl(ethylbenzyl) ammonium chloride (Stepan) (40%) |
| Barquat MS-100 | N-alkyl-N,N-dimethyl-N-benzylammonium chloride (Lonza) (100%) |
| BTC 824 P-100 | N-alkyl-N,N-dimethyl-N-benzyl ammonium chloride (Stepan) (95%) |
| BTC 8358 | N-alkyl-N,N-dimethyl-N-benzyl ammonium chloride (Stepan) (80%) |
| Vantocil 100 | Polyhexamethylenebiguanide (Avecia) |
| Sodium bicarbonate | Sodium bicarbonate (course or fine) (Solvay) |
| Citric Acid | Citric acid (Jungblasauer) |
| Citricoat | Coated citric acid |
| Acusol 771 | Crosslinked polyacrylic acid polymer (Rohm & Haas) |
| Sokolan CP5 | Sodium salt of copolymer of methacrylic acid and maleic anhydride (BASF) |
| Acusol 445 ND | Sodium polyacrylate of molecular weight of 4500 (Rohm & Haas) |
| Optigel SH | Sodium magnesium silicate (Sudchemie) |
| Arbocel TF 30 HG | Amorphous cellulose (Rettenmaier) |
| Sorb-Sol | Amorphous cellulose (Blanver) |
| Sorb-Cel | Amorphous cellulose (Blanver) |
| Arbocel TF 0406 | Amorphous cellulose (Rettenmaier) |
| Polyplasdone XL | Polyvinylpolypyrrolidone (ISP) |
| STPP | Sodium tripolyphosphate |
| Sodium citrate dihydrate | Sodium citrate dihydrate |
| Trisodium citrate dihydrate | Trisodium citrate dihydrate |
| Kyrosan E18 | Starch (Emsland-Starke GmbH) |
| NaOH | Sodium hydroxide |
| Sodium metasilicate | Sodium metasilicate |
| Sodium sulfate | Sodium sulfate |
| Sodium alginate | Sodium alginate |
| Prismalac 40 | Monohydrate lactose (Zetapharm) |
| Karion | Sorbitol (Merck) |
| Fragrance/Fragrance on carrier | Proprietary fragrance (Firmenich) |
| PEG 6000 | Polyethylene glycol with average molecular weight of 6000 (BASF) |
| PEG 4000 | Polyethylene glycol with average molecular weight of 4000 (BASF) |
| PEG 1500 | Polyethylene glycol with average molecular weight of 1500 (BASF) |
| PEG 1450 | Polyethylene glycol with average molecular weight of 1450 (BASF) |
| Catigene T-50 | Didecyldimethyl ammonium chloride (50%) (Stepan) |
| Empilan KM50-PW | Ethoxylated fatty alcohol with 50 moles of ethylene oxide per mole (Rhodia) |
| Magnesium stearate | Magnesium stearate |
| Glucopon 50 G | Alkyl polyglycoside (Cognis) |
| Pluronic F38 | Ethylene oxide/propylene oxide oxide block copolymer containing about 3 moles of propylene oxide condensed with about 8 moles of ethylene oxide (BASF) |
| Pluronic F68 | Ethylene oxide/propylene oxide oxide block copolymer containing 25 to 30 moles of propylene oxide condensed with 33 to 41 moles of ethylene oxide (BASF) |
| Lutensol AT25 | $C_{16-18}$ fatty alcohol ethoxylate (25 moles EO; BASF) |
| Lutensol AT50 | $C_{16-18}$ fatty alcohol ethoxylate (50 moles EO; BASF) |
| Lutensol AT80 | $C_{16-18}$ fatty alcohol ethoxylate (80 moles EO; BASF) |
| Sipernat 22 | Silicone dioxide (Degussa) |
| Microsponge | Microscopic, polymer-based microspheres (Advanced Polymer Systems) |
| Hexylcellosolve on Microsponge | Hexylcellosolve (ethylene glycol hexyl ether) absorbed onto Microsponge |
| Hysorb P7050 | Grafted sodium polyacrylate (BASF) |
| Hysorb P9070 | Grafted sodium polyacrylate (BASF) |
| Hysorb C7055 | Grafted sodium polyacrylate (BASF) |
| Sodium carbonate | Sodium carbonate (coarse, fine or light density) (Solvay) |
| Blue speckles | Proprietary mixture of sodium bicarbonate, acid, and blue dye |
| Valfor 100 | zeolite - Na form (PQ Corporation) |

Certain compositions of Table 1 were tested for antimicrobial activity under European test method EN1276, suspension test, issued by the European Committee for Standardization, Brussels. This test is passed if the bacterial colonies forming units (cfu) are reduced from a $10^7$ cfu (initial level) to a $10^2$ cfu (final level after contact with the disinfecting product), a $10^5$ reduction. The results of the testing are found in Table 3.

TABLE 3

| Example/# of tablets tested | Enterococcus hirae | Escherichia coli | Staphylococcus hirae | Pseudomonas aeruginosa |
|---|---|---|---|---|
| Ex. 17/1* | Pass | Pass | Pass | Fail |
| Ex. 17/2* | Pass | Pass | Pass | Fail |
| Ex. 39/2* | Pass | Fail | Pass | Fail |
| Ex. 40/2* | Fail | Fail | Pass | Fail |
| Ex. 58/2* | Pass | Pass | Pass | N.E.*** |
| Ex. 89/2* | Pass | Pass | Pass | N.E. |
| Ex. 116/1* | Pass | Pass | Pass | Fail |
| Ex. 117/2* | Fail | Pass | Pass | Pass |
| Ex. 211/1** | Pass | Fail | Pass | Fail |
| Ex. 208/1** | Fail | Fail | Fail | Fail |
| Ex. 213/1**** | Borderline***** | Fail | Borderline | N.E. |

*tested in 5 liters of water
**tested in 1 Liter of water
***not evaluated
****tested in 2 liters of water
*****one sample passed/one sample failed In addition, several of the formulations of the present invention were evaluated under established ASTM testing methods for evaluating cleaning efficacy of compositions on masonite wallboard (ASTM D4488 A2) and vinyl tile samples (ASTM D-4488–89 Annex A5) as compared to a control commercially available cleaner, St. Marc antibacterial cleaner (contains non-ionic and cationic surfactants). These testing methods are described below.

The testing protocol according to ASTM D4488 A2 Test Method, which evaluated the efficacy of the cleaning compositions on masonite wallboard samples painted with wall paint, is as follows: The soil applied was a greasy soil sample containing vegetable oil, food shortening and animal fat. The sponge (water dampened) of a Gardner Abrasion Tester apparatus was squirted with a 15 gram sample of a tested cleaning composition, and the apparatus was cycled 10 times. The evaluation of cleaning compositions was "paired" with one side of each of the test samples treated with a composition according to the invention, and the other side of the same sample treated with a comparative example's composition, thus allowing a "side-by-side" comparison to be made. Each of these tests were duplicated on 20 wallboard tiles and the results statistically analyzed.

The cleaning efficacy of the tested compositions was evaluated utilizing a Minolta Chroma Meter CF-110, with Data Processor DP-100, which evaluated spectrophotomic characteristics of the sample.

The testing protocol according to ASTM D4488–89 Annex A5 for particulate soil, which evaluated the efficacy of the cleaning compositions on vinyl tile samples, is as follows: The soil applied was a particulate soil sample containing natural humus, paraffin oil, used crankcase motor oil, Portland cement, silica, lampblack carbon, iron oxide, bandy black clay, stearic acid, and oleic acid. Each of the soiled test vinyl tile samples (two samples) were placed into the apparatus and the center of each tile was wetted with a 20 ml sample of a test formulation and allowed to stand for 1 minute. When approximately 30 seconds had elapsed, a further 50 ml sample was applied to the sponge (water damped, then wrung to remove excess water) of a Gardner Abrasion Tester apparatus. The apparatus was then cycled 10 times, which provided 20 strokes of the sponge across the face of each of the vinyl test tiles. The reflectance values of the cleaned samples were evaluated utilizing a Minolta Chromameter CF-110, with Data Processor DP-100, which evaluated spectrophotomic characteristics of the sample.

TABLE 4

| | Dilution | % Clean |
|---|---|---|
| Cleaning Test A | | |
| 205 | 1 tab/5 L | 12.414%***** |
| 205 | 2 tabs/5 L | 13.040%***** |
| 206 | 1 tab/1 L | 10.689%***** |
| 206 | 1 tab/5 L | 17.266%***** |
| St. Marc | 1 caps*/1 L | 54.749%***** |
| St. Marc | 2 caps/5 L | 45.137%***** |
| Cleaning Test B | | |
| 207 | 1 tab/5 L | 11.431%**** |
| St. Marc | 2 caps/5 L | 39.014%**** |
| Cleaning Test C | | |
| 208 | 1 tab/5 L | 39.514%*** |
| 209 | 1 tab/5 L | 32.777%*** |
| 210 | 1 tab/5 L | 31.524%*** |
| St. Marc | 2 caps/5 L | 30.976%*** |
| Cleaning Test D | | |
| 211 | | |
| 211 | 1 tab/5 L | 11.401** |
| 211 | 2 tabs/5 L | 14.236** |
| St. Marc | 2 caps/5 L | 21.150** |
| Cleaning Test E | | |
| 211 | | |
| 211 | 1 tab/5 L | 12.106** |
| 211 | 2 tabs/5 L | 16.847** |
| St. Marc | 2 caps/5 L | 16.767** |
| Cleaning Test F | | |
| 215 | 1 tab/5 L | 32.39*** |
| 216 | 1 tab/5 L | 28.77*** |
| 217 | 1 tab/5 L | 36.13*** |
| St. Marc | 2 caps/5 L | 26.73*** |
| Cleaning Test G | | |
| 217 | 1 tab/5 L | 38.92****** |
| 218 | 1 tab/5 L | 33.96****** |
| 219 | 1 tab/5 L | 37.19****** |
| 219 | 1 tab/5 L | 33.26****** |
| St. Marc | 2 caps/5 L | 25.40****** |

*a cap is 30 grams.
**average of ten evaluations
***average of five evaluations
****average of three evaluations
*****average of two evaluations
******average of eight evaluations In cleaning test A, B, and C, all formulas are at parity with control. For cleaning tests D and E, formula 211 was not as effective as the control when using 1 tablet/5 L; however, at 2 tablets/5 L, formula 211 is at parity with the control.

While the invention is susceptible of various modifications and alternative forms, it is to be understood that specific embodiments thereof have been shown by way of example which are not intended to limit the invention to the particular forms disclosed; on the contrary the intention is to cover all modifications, equivalents and alternatives falling within the scope and spirit of the invention as expressed in the appended claims.

We claim:

1. A hard surface effervescent cleaning tablet having a homogenous composition consisting of:
    at least 50% wt. of an effervescent agent comprising at least one acidic component, and
    at least one basic component;
    at least one compound having germicidal properties selected from the group consisting of cationic surfactant, biguanides, and phenolics;
    as least one surfacant component selected from the group consisting of non-ionic surfactants, amphoteric surfactant, and optionally one or more components selected from the group consisting of lubricants, colorants, perfumes, deodorizers, preservatives, disintegrants, binders, absorbents, and fillers.

2. The tablet according to claim 1 wherein the compound having germicidal properties is selected from cationic surfactants.

3. The tablet according to claim 1 wherein the compound having germicidal properties is selected from biguanides.

4. The tablet according to claim 1 which further comprises an absorbent.

5. The tablet according to claim 1 which further comprises at least on non-ionic surfactant.

6. The tablet according to claim 1 which further comprises a disintegrant.

7. The tablet according to claim 1 which further comprises a lubricant.

8. An effervescent cleaning tablet having a homogeneous composition consisting of:
    at least 50% wt of an effervescent agent comprising at least one acidic component and at least one basic compound;
    at least one compound having germicidal properties selected from the group consisting of cationic surfactant, biguanides, and phenolics;
    at least one non-ionic surfactant; and
    at least one component selected from the group consisting of amphoteric surfactants, zwitterionic surfactants, lubricants, colorants, perfumes, deodorizers, preservatives, dyes, disintegrants, binders, absorbents, and fillers.

9. The tablet according to claim 8 wherein the compound having germicidal properties is selected from cationic surfactants.

10. The tablet according to claim 8 wherein the compound having germicidal properties is selected from biguanides.

11. The tablet according to claim 8 which further comprises an absorbent.

12. The tablet according to claim 8 which further comprises a disintegrant.

13. The tablet according to claim 8 which further comprises a lubricant.

14. An effervescent cleaning tablet having a homogeneous composition useful for forming a household cleaning and/or disinfecting composition useful for cleaning and/or disinfecting hard surfaces consisting of:
    at least 50% wt of an effervescent agent comprising at least one acidic component, and
    one basic components;
    at least one compound having germicidal, properties selected from the group consisting of cationic surfactant, biguanides, phenolics;
    at least one component selected from the group consisting of non-ionic surfactants, amphoteric surfactants, zwitterionic surfactants, lubricants, colorants, perfumes, deodorizers, preservatives, disintegrants, disinfectants, binders, absorbents and fillers.

* * * * *